(12) United States Patent
Schreuder et al.

(10) Patent No.: US 9,864,144 B2
(45) Date of Patent: Jan. 9, 2018

(54) MULTI-PATH INTERFEROMETERIC SENSOR

(71) Applicant: Octrolix BV, Enschede (NL)

(72) Inventors: Frederik Schreuder, Rijssen (NL); Rene Gerrit Heideman, Oldenzaal (NL)

(73) Assignee: LioniX International BV, Enschede (NL)

(*) Notice: Subject to any disclaimer, the term of this patent is extended or adjusted under 35 U.S.C. 154(b) by 23 days.

(21) Appl. No.: 15/015,965

(22) Filed: Feb. 4, 2016

(65) Prior Publication Data

US 2016/0265898 A1 Sep. 15, 2016

Related U.S. Application Data

(60) Provisional application No. 62/111,776, filed on Feb. 4, 2015.

(51) Int. Cl.
| | | |
|---|---|---|
| *G01D 5/26* | (2006.01) | |
| *G02B 6/293* | (2006.01) | |
| *G01N 21/45* | (2006.01) | |
| *G01N 21/77* | (2006.01) | |
| *G01N 21/39* | (2006.01) | |

(52) U.S. Cl.
CPC ......... *G02B 6/29343* (2013.01); *G01N 21/45* (2013.01); *G01N 21/7746* (2013.01); *G02B 6/29355* (2013.01); *G01N 2021/399* (2013.01); *G01N 2021/7716* (2013.01); *G01N 2021/7776* (2013.01); *G01N 2021/7779* (2013.01)

(58) Field of Classification Search
CPC ............ G01B 9/02027; G01B 9/02028; G01D 5/266; G01D 5/353; G01D 5/35329
USPC ........................................................ 356/478
See application file for complete search history.

(56) References Cited

U.S. PATENT DOCUMENTS

| | | | | |
|---|---|---|---|---|
| 4,697,926 A | * | 10/1987 | Youngquist | G01D 5/35383 250/227.12 |
| 4,770,535 A | * | 9/1988 | Kim | G01D 5/35383 250/227.27 |
| 5,663,790 A | * | 9/1997 | Ekstrom | G01N 21/41 204/452 |
| 6,721,053 B1 | * | 4/2004 | Maseeh | G01N 21/7746 356/436 |
| 2010/0014544 A1 | * | 1/2010 | Heideman | H01S 5/065 372/20 |
| 2016/0282184 A1 | * | 9/2016 | Khalil | G01J 3/108 |

* cited by examiner

*Primary Examiner* — Jonathan Hansen
(74) *Attorney, Agent, or Firm* — Kaplan Breyer Schwarz, LLP

(57) ABSTRACT

A multi-path interferometric sensor for sensing small changes in the refractive index of sensing arms thereof, such as caused by the presence of an analyte or changes in analyte concentration, is disclosed. The sensor includes a single light source, a single detector, and a plurality of interferometers or a single multi-path interferometer. The various sensing branches within the multi-path interferometric sensor each include a delay having a different length. This results in a different modulation frequency for each interferometer, each of carriers include phase information that correlates to a change in refractive index and, ultimately, analyte concentration. The plural carrier frequencies enable simultaneous detection of multiple samples.

13 Claims, 8 Drawing Sheets

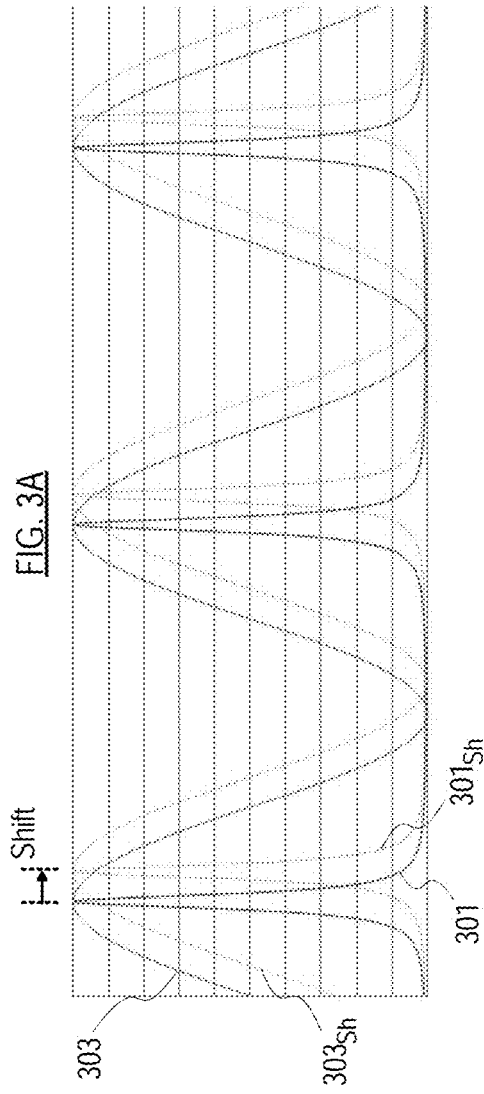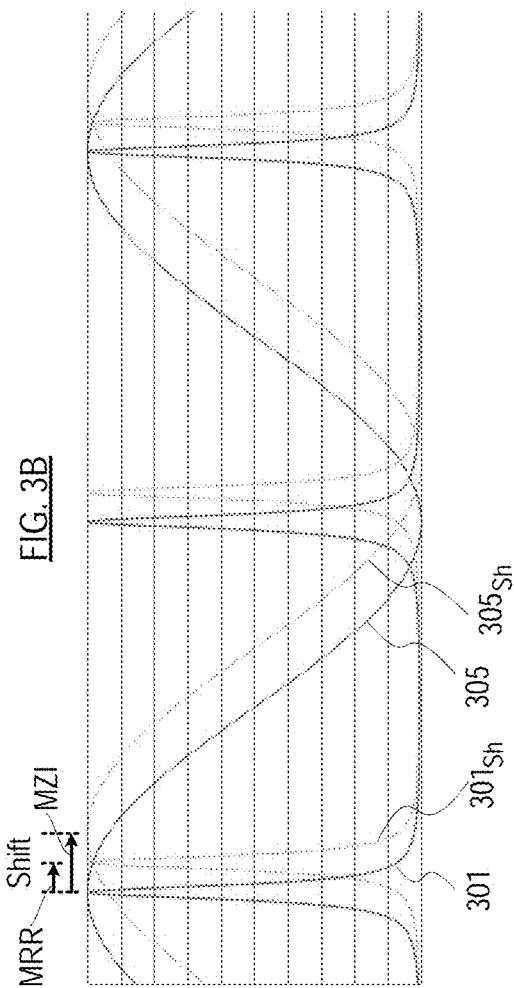

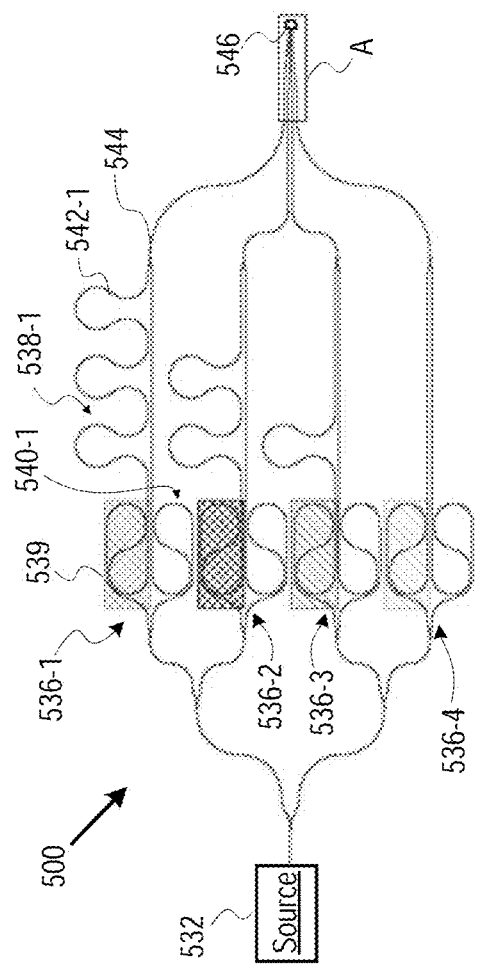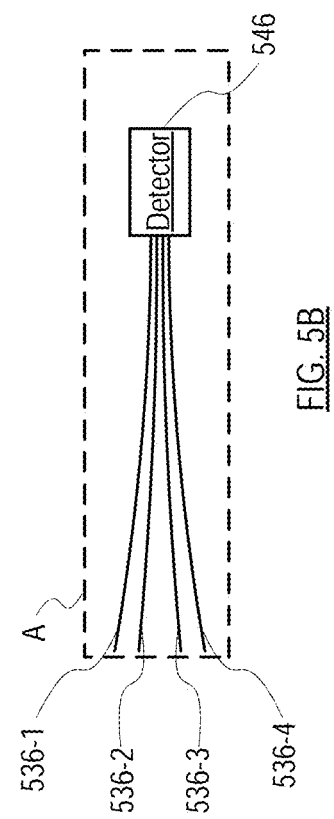

MULTI-PATH INTERFEROMETERIC SENSOR

STATEMENT OF RELATED CASES

This case claims priority of U.S. Pat. App. Ser. No. 62/111,776, which was filed on Feb. 4, 2015 and is incorporated by reference herein.

FIELD OF THE INVENTION

The present invention relates generally to refractive index sensors.

BACKGROUND OF THE INVENTION

An interferometer can be used as a highly sensitive refractive index sensor. In some sensing applications, a change in the effective refractive index of the waveguide is induced by a change in the concentration of an analyte that is present on the surface of waveguide.

SUMMARY OF THE INVENTION

The invention provides a multi-path interferometric sensor and a method for sensing a change in the refractive index of sensing arms of the sensor. The sensor can be used, for example and without limitation, to determine the concentration of plural samples of biological or chemical analytes.

In accordance with the illustrative embodiment, a multi-path interferometric sensor includes a single light source, one or more detectors, and a plurality of interferometers or a single multi-path interferometer (hereinafter these terms are used interchangeably unless specifically noted). In the illustrative embodiment, the light source is a VCSEL (vertical-cavity surface-emitting laser), the interferometers are asymmetric Mach-Zehnder interferometers, and the detector is a photodiode. In some embodiments, the elements of the integrated optical sensor are fully integrated to form a photonic lightwave circuit.

The interferometers are formed as surface waveguides using any waveguide technology (e.g., silica-on-silicon, silicon, nitride-based, etc.). In some embodiments, individual interferometers or arms of the multi-path interferometric sensor each serve as a sensor for sensing the refractive index of a medium and, ultimately, the concentration of an analyte.

In some embodiments, a sensing window is created by thinning a portion of one of the arms/branches of each interferometer of the multi-path interferometric sensor. The branch having the sensing window functions as a sensing branch and the other branch functions as a reference branch. In some other embodiments, for example but not necessarily when a biochemical coating (selective interface layer) is present on the sensing branch, both arms are thinned.

When exposed to an analyte (typically, but not necessarily, carried in a liquid), the analyte effectively becomes part of the cladding of the waveguides of the asymmetric interferometers. Due to the thinning of the cladding in the portion of the sensing branch, the presence of the analyte will have a disparate effect on the refractive index of the cladding in the sensing and reference branches. The presence of, or increases/decreases in the concentration of, an analyte on the sensing-branch waveguide induces a change in the effective refractive index (of the cladding of the waveguide). This change in effective refractive index alters the optical path length for the signal and results in a phase shift of a signal propagating through the asymmetric interferometer. The interferometers can very accurately measure the resulting phase shift and correlate it to the presence and/or concentration of an analyte.

For phase detection, a frequency-based method is used. In some embodiments, multiple y-splitters are used to divide the input signal from the single source into an appropriate number of signals for launching into plural asymmetric interferometers. The various sensing branches within the multi-path interferometric sensor each include a delay having a different length. This results in a different modulation frequency for each interferometer of the multi-path interferometric sensor.

The individual signals from the various interferometers of the multi-path interferometric sensor will interfere and, in some embodiments, are recombined into a single output channel via y-combiners. This results in a combined sinusoidal signal containing the individual modulation frequencies and the difference frequencies between the interferometers. In some alternative embodiments, other elements are used for signal splitter and/or recombination, such as, without limitation, MMI couplers and directional couplers.

In the illustrative embodiment, the single output channel is fed to a single detector. In some alternative embodiments, multiple detectors are used, typically (although not necessarily) when the output signals are not combined to form a single output channel. The frequency output of the device is predictable and only the frequencies of interest are selected for phase information. This architecture enables a sensor with the ability to sense plural samples using a single optical source and a single detector, thereby resulting in a very compact device.

This approach of creating multiple modulation frequencies in the wavelength domain by tuning the free spectral range of each interferometer to enable simultaneous detection of multiple samples is not only applicable to aMZIs. In some other embodiments, other asymmetric interferometer layouts, such as Michelson, etc., can suitably be used. In yet some further embodiments, plural micro ring resonators can be used as sensors for such a system.

In some embodiments, each sensing window in each of the asymmetric interferometers is exposed to the same medium (i.e., same analyte, same concentration). The information obtained from each asymmetric interferometer is processed to obtain a single estimate of analyte concentration. This is expected to improve the accuracy of the estimate or decrease the variance in the estimates as compared to the estimate from a single asymmetric interferometer.

In embodiments in which the integrated optics sensor is intended to monitor plural samples that differ as to the type of analyte, there must be some way to ensure that each sensing branch senses a different analyte. In some embodiments, this is accomplished by fluidically isolating the sensing branches of the various interferometers of the multi-path interferometric sensor. This can be done, for example, by situating each asymmetric interferometer in a different one of a plurality of micro-channels that are fluidically isolated from one another. A different analyte-containing sample is introduced into each micro-channel.

In some other embodiments, the asymmetric interferometers are rendered sensitive to a different analyte. For example, the various asymmetric interferometers can have their claddings surface-functionalized so that they are selective for a particular analyte. In some further embodiments, the sensing branches are both fluidically isolated and surface functionalized.

For applications in which the analyte is present in a gas, the sensing branch is appropriately functionalized to capture (e.g., absorb, etc.) the analyte.

The foregoing brief summary summarizes some features of some embodiments of the present invention. It is to be understood that many variations of the invention are possible, and that the scope of the present invention is defined by the claims accompanying this disclosure in conjunction with the full text of this specification and the accompanying drawings.

BRIEF DESCRIPTION OF THE DRAWINGS

FIG. 3A depicts the wavelength responsivity of the sensors of FIG. 1A and FIG. 1B wherein the FSR of the first sensor and the second sensor are the same.

FIG. 3B depicts the wavelength responsivity of the sensors of FIG. 1A and FIG. 1B wherein the FSR of the first sensor is twice as large as that of the second sensor.

FIG. 5A depicts a second embodiment of a multi-path interferometric sensor in accordance with the present invention and FIG. 5B depicts how four signals, rather than one signal as in the embodiment of FIG. 4, is provided to the detector.

DETAILED DESCRIPTION

The present invention provides a multi-path interferometric sensor useful, for example, for determining changes in the concentration of an analyte or the presence of an analyte. The sensor is capable of simultaneously sensing multiple samples.

When an analyte (typically but not necessarily present in a liquid medium) is disposed on a waveguide, it effectively forms a portion of the waveguide's cladding. Consequently, increases or decreases in the concentration of the analyte induce a change in the effective refractive index of the cladding of the waveguide. This change in effective refractive index results in a small difference in optical path length of a signal propagating through the waveguide. This change in optical path length can result in a phase shift that can be very accurately measured by the interferometer.

Figure 1A:
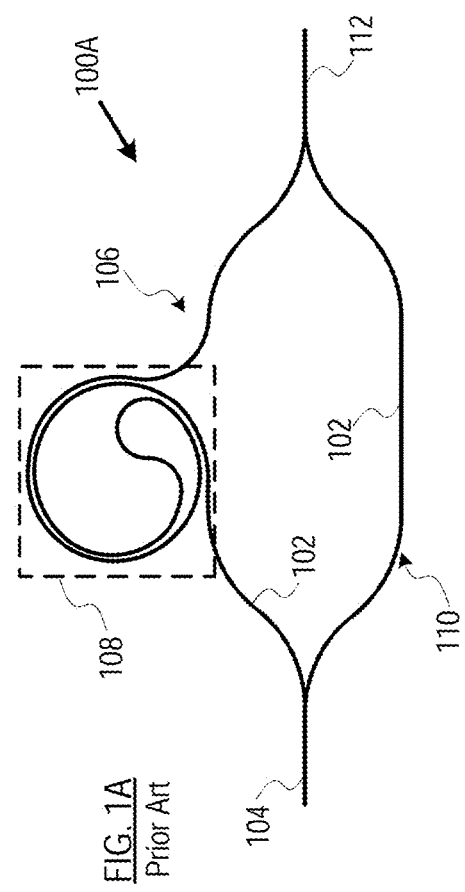
FIG. 1A depicts a first conventional interferometric sensor comprising an asymmetric Mach-Zehnder interferometer.
Figure 1B:
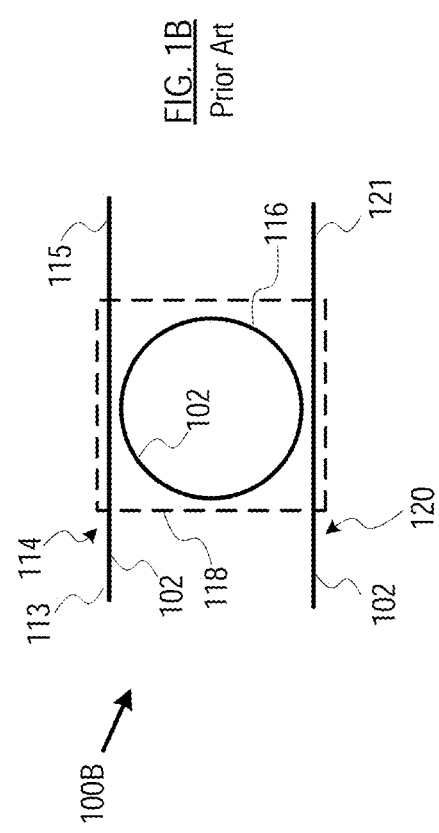
FIG. 1B depicts a second conventional interferometric sensor comprising a micro-ring resonator.

FIGS. 1A and 1B depict a portion of conventional interferometric sensors. Sensor 100A depicted in FIG. 1A is based on an asymmetric Mach Zehnder interferometer (aMZI) and sensor 100B depicted in FIG. 1B is based on a micro-ring resonator (MRR).

Sensor 100A is formed from surface waveguides 102 and has input 104 and output 112. The sensor includes reference branch 110 and sensing branch 106. The sensing branch includes sensing window 108. Sensor 100B is also formed from surface waveguides 102 in the form of two bus waveguides 114 and 120 that flank sensing "branch" 116, which is configured as a loop waveguide. Bus waveguide 114 includes input 113 and through port 115. Bus waveguide 120 includes drop port 121. Sensing branch 116 includes sensing window 118. It is notable that the theory and principles presented for the aMZI and MRR, as presented below, are applicable to all types of interferometers.

The presence of an analyte on waveguide 102 within sensing window 108 of sensor 100A results in a change in refractive index of the waveguide in that region. Likewise, the presence of an analyte on waveguide 102 within sensing window 118 of sensor 100B results in a change in refractive index. This change in refractive index results in a small change in optical path length (OPL) for a signal traveling through the waveguide.

Using an interferometer, the phase shift of a signal undergoing a small change in OPL between the two branches of the interferometer can be very accurately measured. The phase shift results in constructive and deconstructive interference. For a single-branch waveguide, the optical path length is defined as OPL and is proportional to the effective refractive index ($N_{eff}$) and the length (L) of the waveguide. The resulting phase change ($\varphi$) depends on OPL and wavelength.

$$OPL = L \cdot N_{eff} \quad [1]$$

$$\varphi = 2\pi/\lambda_0 \cdot L \cdot N_{eff} \quad [2]$$

Definitions: $\lambda_o = \lambda \cdot N_{eff}$ and $v_{Phase} = c/N_{eff}$ and
$$f = v_{phase}/\lambda \quad [3]$$

wherein: c=speed of light

In sensor 100A, wherein the interferometer is an aMZI, there is a difference, δOPL, in optical path length between the two branches:

$$\delta OPL = OPL_{Sens} - OPL_{Ref} = L_{Sens} \cdot N_{eff(Sens)} - L_{Ref} \cdot N_{eff(Ref)} \quad [4]$$

The phase difference, δφ, due to the difference in optical path length is given by:

$$\delta\varphi_{mzi} = 2\pi/\lambda_o \cdot OPL_{Sens} - 2\pi/\lambda_o \cdot OPL_{Ref} \quad [5]$$

In sensor 100B, wherein the interferometer is an MRR, there is also a difference in optical path length δOPL. In particular, an MRR can be conceptualized as an MZI having a reference branch with a length of zero. The difference in path length for an MRR is therefore given by:

$$\delta OPL = CPL_{Sens} - OPL_{Ref} = OPL_{Sens} = OPL_{Ring} = L_{Ring} \cdot N_{eff} \quad [6]$$

For the MRR the phase difference, δφ, or "round trip phase" is given by:

$$\delta\varphi_{Ring} = 2\pi/\lambda_o \cdot OPL_{Ring} \quad [7]$$

Sensors 100A and 110B both experience the same phase change when:

$$\delta OPL = OPL_{Ring} = OPL_{Sens} \text{ and } OPL_{Ref} = 0$$

In this case, the asymmetry for both sensors is the same with asymmetry defined by the optical path length difference δOPL.

Interference Condition.

For both sensor 100A with the aMZI and sensor 100B with the MRR, constructive interference occurs when the wavelength fits a whole number of times within the interferometric part, with "M" being the order of interference.

$$\varphi = 2\pi \cdot M \quad [8]$$

$$M = \delta OPL/\lambda_{o(M)} \quad [9]$$

$$M = \delta OPL \cdot f_M/c \quad [10]$$

Thus, each resonance condition of the MRR and the aMZI occurs at the same interval when the aMZI has maximum constructive interference when:

$$\delta OPL = OPL_{Ring} = OPL_{Sens} \text{ and } OPL_{Ref} = 0 \quad [5]$$

Figure 2:
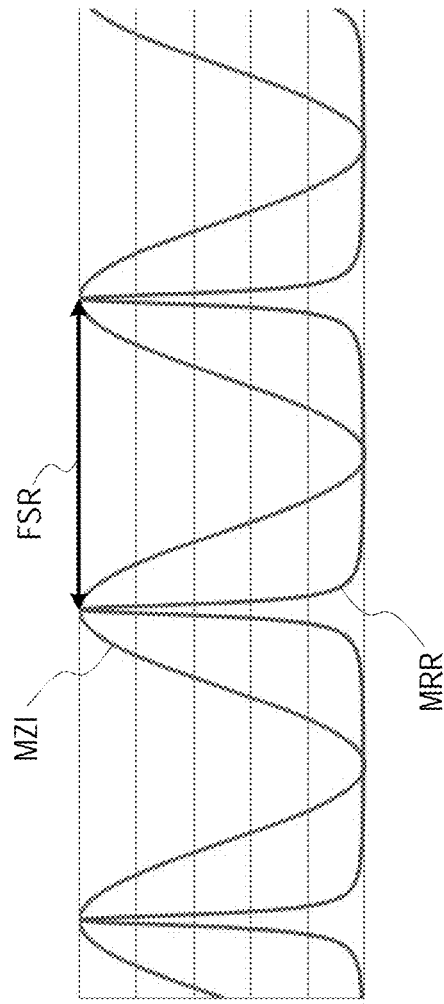
FIG. 2 depicts the spectral responses of the sensors of FIG. 1A and FIG. 1B.

This can be seen from the plot of spectral response shown in FIG. 2. The distance between two resonance conditions is called the Free Spectral Range (FSR), which corresponds to 1 period/fringe phase change.

At a certain wavelength $\lambda_{o(m)}$, the interferometric part has M orders of interference. The FSR in the wavelength range is the difference between $\lambda_{o(m)}$ and $\lambda_{(0m+1)}$. Using expressions [9] and [10] for the frequency domain, FSR is expressed as follows:

$$FSR_\lambda = \lambda_{o(M)}/(M+1) = \lambda_{o(M)}^2/(\delta OPL + \lambda_{o(M)}) \approx \lambda_{o(M)hu\ 2}/\delta OPL; \delta OPL >>> \lambda_{o(M)} \quad [11]$$

$$FSR_f = f_M/M = c/\delta OPL \quad [12]$$

As indicated above, the FSR of an MRR and an aMZI is equal when $\delta OPL = OPL_{ring} = OPL_{Sens}$ and $OPL_{ref} = 0$, as per FIG. 2.

Relation Between Wavelength Shift and Optical Path Length When Using Asymmetric Interferometers to Measure Small Changes in Refractive Index.

The frequency (1 period=FSR) is considered constant for a certain design, but the change in phase of this frequency corresponds with a small change in path length difference. Expression [8] and are rearranged to obtain the shift in wavelength $\Delta\lambda_{o(M)}$ of the mth order of interference condition. The mth order of interference can also be expressed in terms of wavelength $\lambda 0_m$ and the $FSR_\lambda$ and equivalently in the frequency domain. Since, per expression [11], $FSR_\lambda = \lambda_{o(M)}/(M+1)$:

$$\Delta\lambda_{o(M)} = \Delta(\delta OPL)/M = \Delta(\delta OPL) \cdot FSR_\lambda/\lambda_{o(M)} = L_{Sens} \cdot \Delta(N_{eff(Sens)}) \cdot FSR_\lambda/\lambda_{o(M)}; M >> 1 \quad [13]$$

$$\Delta f_M = M \cdot c/(\Delta((\delta OPL)) = f_M \cdot c/(\Delta(\delta OPL) \cdot FSR_f) = f_M \cdot c/(L_{Sens} \cdot \Delta(N_{eff(Sens)}) \cdot FSR_f) \quad [14]$$

Rearranging expressions [13] and [14] in terms of $L_{Ref}$ and $L_{Sens}$ gives:

$$\Delta\lambda_M = \Delta(\delta OPL)/M = \lambda_{o(M)} \cdot L_{Sens} \cdot \Delta(N_{eff(Sens)})/L_{Sens} \cdot N_{eff(Sens)} - L_{Ref} \cdot N_{eff(Ref)}) \quad [15]$$

$$\Delta f_M = f_M \cdot \Delta(\delta OPL)/(L_{Sens} \cdot \Delta(N_{eff(Sens)})) \quad [16]$$

$$\Delta f_M = f_M \cdot (L_{Sens} \cdot N_{eff(Sens)} - L_{Ref} \cdot N_{eff(Ref)})/(L_{Sens} \cdot \Delta(N_{eff(Sens)})) \quad [17]$$

In the MRR embodiment, $L_{Ref} = 0$. This simplifies expressions [15]-[17] and shows that a shift $\Delta\lambda_{o(M)}$ in wavelength does not depend on the length of the sensing branch, $L_{Sens}$.

$$\Delta\lambda_M = \lambda_{o(M)} \cdot \Delta(N_{eff(Sens)})/N_{eff(Sens)} \quad [18]$$

$$\Delta f_M = f_M \cdot N_{eff(Sens)}/(\Delta(N_{eff(Sens)})) \quad [19]$$

Based on the foregoing, it is concluded that:

Expression [13] shows that the amount of wavelength shift, $\Delta\lambda_{o(M)}$, depends on the change in optical path length, $\Delta(\delta OPL)$, and is inversely proportional with the mth order of interference.

A low order interference results in a larger spectral shift, $\Delta\lambda_{o(M)}$, compared to a higher mth order of interference for the same change in optical path length, $\Delta(\delta OPL)$.

The spectral shift, $\Delta\lambda_{o(M)}$, of an MRR is equal to the spectral shift, $\Delta\lambda_{o(M)}$, of an aMZI when $\delta OPL = OPL_{ring} = OPL_{Sens}$ and $OPL_{ref} = 0$.

The responsivity of an MRR in terms of wavelength shift per $\Delta(N_{eff(Sens)})$ is fixed. Wavelength shift is $\Delta\lambda_{o(M)}$ regardless of the size of ring.

The responsivity of am aMZI in terms of wavelength shift per $\Delta(N_{eff(Sens)})$ is not fixed. A change in the length $L_{Sens}$ of the sensing branch or a change in the length $L_{Ref}$ of the reference branch changes the responsivity.

As a consequence of the foregoing, responsivity in terms of wavelength shift per $\Delta(N_{eff(Sens)})$ for the aMZI is better or equal to the MRR when:

$$OPL_{Sens} \geq OPL_{ring} \text{ and } FSR_\lambda^{aMZI} \geq FSR_\lambda^{ring}$$

For an MRR, an increase of the sensing window to $OPL_{Sens} = OPL_{ring}$ has no effect on the responsivity since it will also increase the free spectral/mode order. On balance, there will be no increase of the responsivity. For an aMZI, however, an increase of the $OPL_{Sens}$ can result in an increase of responsivity. Since is because the free spectral range/mode order can be adjusted.

The differing responsivity behavior for an aMZR and an MRR, in terms of wavelength shift per $\Delta(N_{eff(Sens)})$, is illustrated via FIGS. 3A and 3B. In particular, these figures show the spectral response of MRR signal 301 in the drop port, wherein the MRR has a certain FSR and the length of ring, $L_{Ring}$, is equal to the length, $L_{Sens}$, of the sensing branch. FIG. 3A also shows the spectral response of an aMZI signal 303 for an aMZI having the same FSR as the MRR and wherein the length, $L_{Sens}$, of the sensing branch of the aMZI is equal to the length of the ring and wherein the length of the reference branch equals zero. In FIG. 3B, aMZI signal 305 for an aMZI having an FSR twice that of the MRR, but wherein the length of the sensing branch of the aMZI and the MRR are equal, as for FIG. 3A.

A change in $\Delta(N_{eff(Sens)})$ is then applied. In FIG. 3A, wherein the MRR and the aMZI have a sensing branch of the same length and identical FSR, the resulting wavelength shift of the MRR signal ($301_{Sh}$) and the aMZI signal ($303_{Sh}$) is identical. However, in FIG. 3B, wherein the aMZI has an FSR twice that of the MRR, the lower order of interference (i.e., 2×FSR) results in a spectral shift of aMZI signal $305_{Sh}$ that is twice as large as that of MRR signal $301_{Sh}$. Effectively, the same change in phase is spread over a larger wavelength range, therefore improving the accuracy of the readout.

It is notable that the improvement in responsivity is valid for a wavelength scanning technique, which is used in embodiments of the present invention. If phase is determined via signal amplitude, the conclusions/results will be different. For wavelength scanning, it is relatively more important to reduce wavelength noise and there is relatively less concern about random noise in the signal intensity. High Q-factors, for example, are a way to improve resolution, but this applies to an amplitude scanning system, not for wavelength scanning as in embodiments of the invention.

In some embodiments of the invention, an 850 nm (+/−10 nm) VCSEL-based scanning system is used, which enables scanning a wavelength span of about 3 nanometers. The 850 nm VCSEL is used because it is currently available at low cost, is single mode, and has a single and fixed stable linear polarization. However, a light source (VCSEL or otherwise) having any wavelength in the visible range or in the infrared range may suitably be used. As will be appreciated by those skilled in the art, the waveguide geometry/cross section must be designed for the target wavelength. In general, the use of a light source have a relatively shorter wavelength will result in better sensitivity for the multi-path interferometric sensor.

VCSELs, as well as several other scanning light sources, usually exhibit a slightly different wavelength response curve from die to die. Typically, they are not linear with current and depend on VCSEL temperature and modulation speed. As a consequence, for use in conjunction with embodiments of the invention, the relative VCSEL wavelength output must be calibrated to ensure accurate measurement results.

A static measurement in advance of the VCSEL with a spectral analyzer is not useful. This is because the wavelength output changes when the VCSEL is modulated quickly. At a high scan rate, accurate measurements with a spectral analyzer are very problematic. This problem is addressed, in some embodiments, using a known a-MZI structure to linearize the VCSEL output.

In accordance with an embodiment, the periodicity of the aMZI that is to be used for calibration is statically measured via a standard spectral analyzer. A linear scan of VCSEL current is then performed. This typically results in a chirped response curve of the MZI. Since the periodicity of the aMZI has already been determined, once can readily determine how to adjust the current to obtain a linear frequency response (i.e., a perfect sine wave). Thus, knowing aMZI periodicity, the scanning range of the VCSEL can be accurately determined based on the amount of periods measured.

The signal from the aMZI sensor could itself be used to verify on an ongoing basis that the signal wavelength response remains linear. In some embodiments, an additional default calibration structure on the chip is used since the response will vary minimally from chip to chip and would only require one calibration with a spectral analyzer to determine the response of such a structure.

In this fashion, the relative wavelength response of the dynamic scanning system can be determined and monitored. Although the scanning system was discussed in the context of a VCSEL, other sources can be used.

Embodiments of a Multi-path Interferometric Sensor in accordance with the Present Teachings.

An aMZI applies an amplitude modulation on the input as function of light frequency. With a linear light frequency sweep this modulation will result in a single-frequency sinusoidal modulation with a phase determined by the sweep starting frequency and by the aMZI. Frequency-domain-based detection algorithms are used to determine this phase. In the illustrative embodiment, phase detection of the aMZI is performed using a frequency-based detection method based on a linear least squares error fitting. Such an approach is advantageous because using this algorithm in combination with the orthogonal sinoidal signal provides a minimum error condition that is always the same for a certain frequency. As a consequence, an iterative procedure is not required, so that the algorithm is very fast, accurate, and even facilitates the otherwise computationally intensive analysis for arrays of rings.

In accordance with the present teachings, input light from a single source is split between multiple aMZIs or by using a multi path interferometer. In the illustrative embodiment, the light is split using Y-splitters, but in other embodiments, MMI couplers, directional couplers, etc., may suitably be used. Each aMZI has a different frequency by adjusting the FSR. The signals from the multiple aMZIs or multi-path interferometer are ultimately combined and measured at a single detector. Information from each individual modulation frequency is extracted to determine phase. It is important that the overlap of modulation frequencies is negligible.

FIGS. 4 through 8 depict various embodiments of a multi-path interferometric sensor (either plural aMZIs or a single multi-path interferometer). The phase information associated with each modulation frequency, as results from the design of each interferometer/sensing branch, can be extracted and analyzed in accordance with the present teachings.

The sensors depicted in FIGS. 4 through 8 each include four interferometers or three sensing branches and one reference branch. It will be understood that embodiments of a multi-path interferometric sensor in accordance with the present teachings can include more interferometers/sensing branches or fewer interferometers/sensing branches than what is shown in FIGS. 4 through 8. In light of the present disclosure, those skilled in the art will be able to make and use such alternative embodiments.

Figure 4:
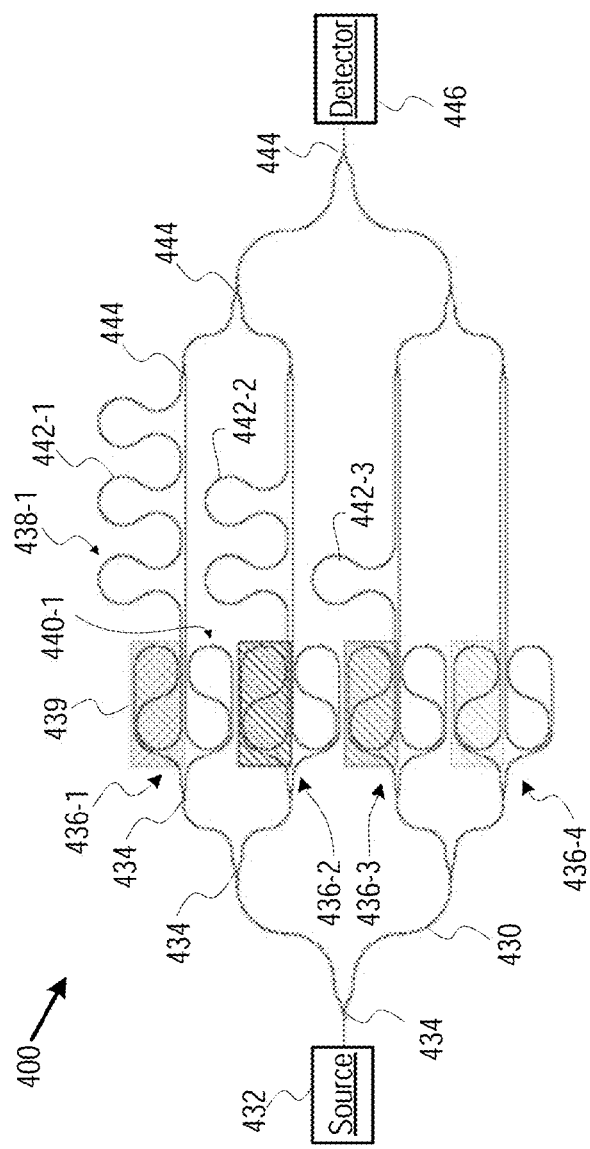
FIG. 4 depicts a first embodiment of a multi-path interferometric sensor in accordance with the present invention.

FIG. 4 depicts multi-path interferometric sensor 400 comprising three asymmetric mach-zehnder interferometers 436-$i$, i=1 to 3 and one symmetric mach-zehnder interferometer 436-4 (collectively "interferometer(s) 436") implemented in surface waveguides 430. Sensor 400 includes a single optical source 432, which in the illustrative embodiment is a VCSEL, and a single detector 446, which is a photodiode. To deliver light from source 432 to interferometers 436, a series of y-splitters 434 are used.

Each interferometer 436 includes a sensing branch 438-$i$, i=1 to 4 and a reference branch 440-$i$, i=1 to 4. Each sensing branch 438-$i$ includes sensing window 439 The sensing branch 438-$i$ of each of asymmetric interferometers 436-1 through 436-3 includes respective delay 442-$i$, i=1,3. In the embodiment depicted in FIG. 4, the delay 442-$i$ for each interferometer is different, as represented by the different number of partial loops. These different delays (or "zero" delay in the case of 436-4) result in a different modulation frequency for each of the four interferometers. As previously discussed, this enables the phase information associated with each modulation frequency (and hence each interferometer) to be extracted and analyzed.

The signals from the two branches of each interferometer 436 are combined via y-combiners 444 and, in turn, the signals from each interferometers are combined by y-combiners 444 to provide a single signal at detector 446. This will cause interference between all possible paths that the light can follow through sensor 400. As long as the lengths of each path are properly chosen as discussed above, the signals can be separated in the frequency domain for analysis.

FIG. 5A depicts multi-path interferometric sensor 500. This sensor is similar in architecture to sensor 400. In particular, sensor 500 includes three asymmetric mach-zehnder interferometers 536-$i$, i=1 to 3 and one symmetric mach-zehnder interferometer 536-4 (collectively "interferometer(s) 536"). Like sensor 400, sensor 500 includes a single optical source 532, which in the illustrative embodiment is a VCSEL, and a single detector 546, which is a photodiode. To deliver light from source 532 to interferometers 536, a series of y-splitters 534 are used.

Each interferometer 536 includes a sensing branch 538-$i$, i=1 to 4 and a reference branch 540-$i$, i=1 to 4. Each sensing branch 538-$i$ includes sensing window 539 The sensing branch 538-$i$ of each of asymmetric interferometers 536-1 through 536-3 includes respective delay 542-$i$, i=1,3, which is different for each interferometer.

Rather than merging all signals to provide a single signal to detector 446, sensor 500 provides four signals—one from each interferometer 536 to detector 546, as best shown in FIG. 5B.

Figure 6:
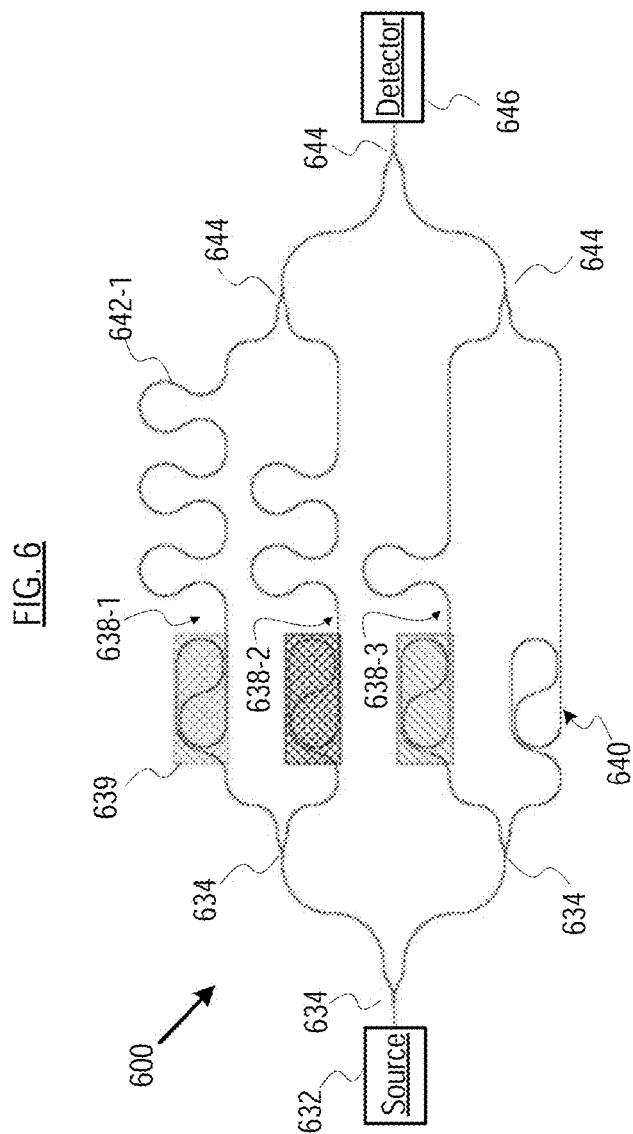
FIG. 6 depicts a third embodiment of a multi-path interferometric sensor in accordance with the present invention.

FIG. 6 depicts multi-path interferometric sensor 600. Sensor 600 includes three sensing branches 638-$i$, i=1 to 3, each of which includes sensing window 639. Each sensing branch 638-*i* includes respective delay 642-*i*, i=1,3, which is different for each sensing branch.

Like sensors 400 and 500, sensor 600 includes a single optical source 632, which in the illustrative embodiment is a VCSEL, and a single detector 646, which is a photodiode. To deliver light from source 632 to the sensing and reference branches, a series of y-splitters 634 are used.

Multi-path interferometric sensor 600 differs from sensor 400 in that rather than having an reference branch for each sensing branch, sensor 600 uses shared reference branch 640. Sensor 600 differs from sensor 500 in the same manner (as sensor 400) and, in addition, sensor 600 provides a merged signal to detector 646.

Figure 7:
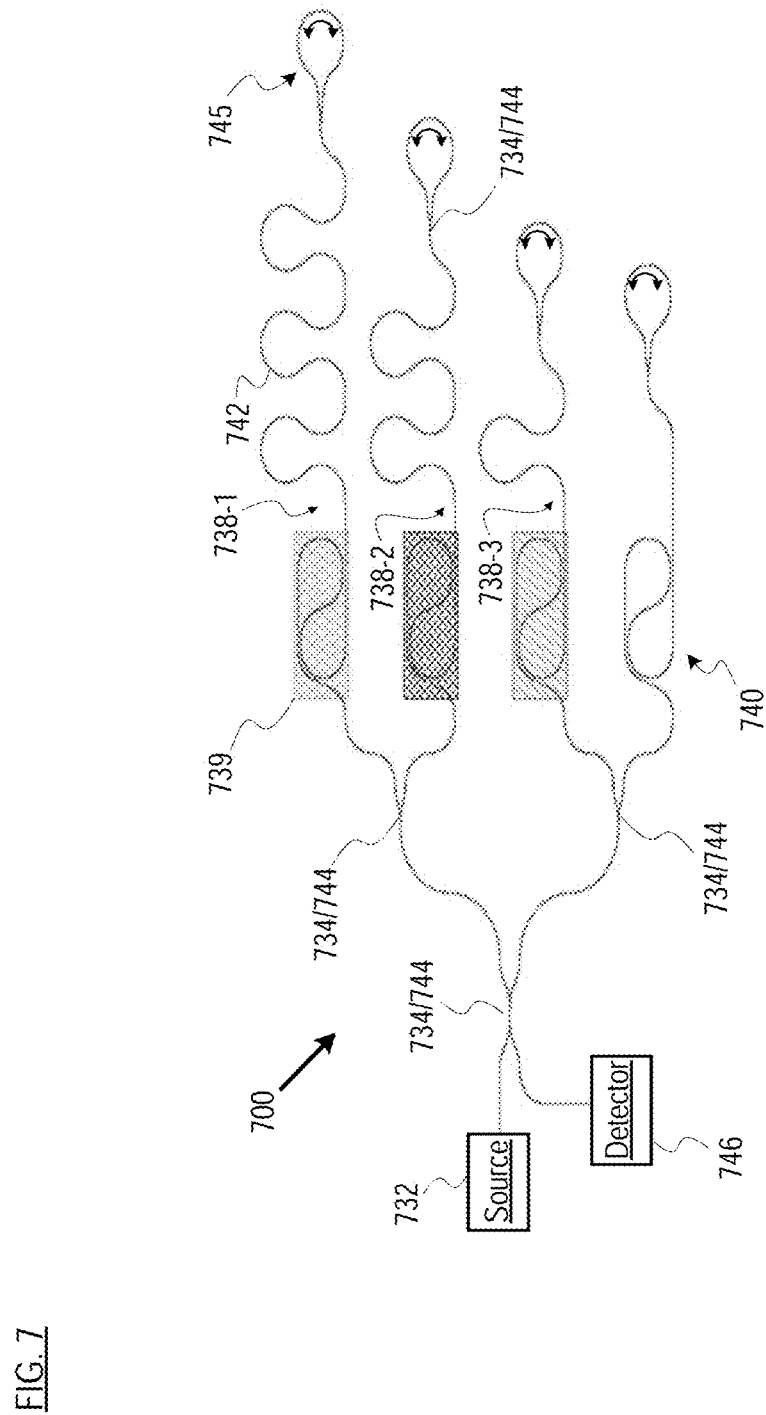
FIG. 7 depicts a fourth embodiment of a multi-path interferometric sensor in accordance with the present invention.

FIG. 7 depicts multi-path interferometric sensor 700. Sensor 700 is similar to sensor 600 in that it provides three sensing branches 738-*i*, i=1 to 3, each of which includes sensing window 739. Each sensing branch 738-*i* includes respective delay 742-*i*, i=1,3, which is different for each sensing branch.

Like sensors 400, 500, and 600, sensor 700 includes a single optical source 732, which in the illustrative embodiment is a VCSEL, and a single detector 746, which is a photodiode. Unlike sensors 400, 500, and 600, sensor 700 is arranged in a Michelson layout wherein loop 745 is disposed at the end of each sensing and reference branch. This effectively doubles the length of each branch. Sensor 700 includes y-splitters/combiners 734/744 to split or combine the signals propagating through the branches. Sensor 700 provides a merged signal to detector 746.

Figure 8:
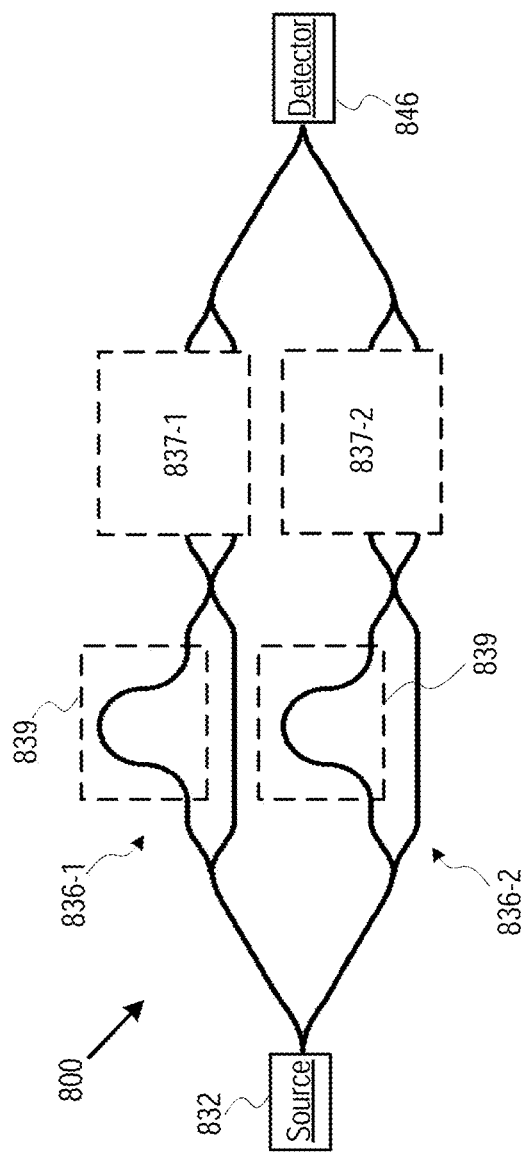
FIG. 8 depicts a fifth embodiment of a multi-path interferometric sensor in accordance with the present invention.

FIG. 8 depicts multi-path interferometric sensor 800. This sensor includes four interferometers 836-1, 836-2, 837-1, and 837-2. Interferometers 836-1 and 836-2 are identical to one another. Interferometers 837-1 and 837-2 have a path length difference that is at least three times longer than interferometers 836-1/836-2. Furthermore, the length of the sensing branch of 837-1 and 837-2 is different from one another.

In sensor 800, interferometers 836-1 and 836-2 are used for sensing, and include sensing window 839. Interferometers 837-1 and 837-2 are used to create the modulation frequency. As a consequence, the signal that is output from interferometer 836-1 is modulated with the modulation frequency created by interferometer 837-1. This results, in the frequency domain, in peaks at the carrier frequencies associated with 836-1, 837-1, 836-1 minus 837-1, and 837-1 plus 836-1. Likewise, the signal that is output from interferometer 836-2 is modulated with the modulation frequency created by interferometer 837-1. And this results, in analogous fashion, in peaks at the carrier frequencies associated with 836-2, 837-2, 836-2 minus 837-2, and 837-2 plus 836-2.

An advantage of sensor 800 is that all of the sensing structures can be identical to one another.

What is claimed:

1. A multi-path interferometric sensor comprising:
   a single light source for producing an optical signal, wherein the light source is suitably configured for wavelength scanning through a range of wavelengths on a periodic basis;
   surface waveguides defining a plurality of interferometers, wherein:
   a) each interferometer includes a sensing branch and a reference branch, each of which sensing branch and reference branch receive a portion of the optical signal;
   b) each sensing branch includes a sensing window in which a portion of a cladding of the waveguide defining the sensing branch is thinned relative to the cladding of the waveguide defining the reference branch;
   c) each sensing branch has a length that is different from one another;
   d) the portion of the optical signal received by each interferometer is characterized by a different modulation frequency as a consequence of the different length of the sensing branch of each interferometer; and
   a detector for receiving the portion of the optical signal from each interferometer.

2. The multi-path interferometric sensor of claim 1 wherein the single light source is a vertical cavity surface emitting laser.

3. The multi-path interferometric sensor of claim 2 wherein the vertical cavity surface emitting laser emits light at a wavelength of 850 nanometers+/−10 nanometers.

4. The multi-path interferometric sensor of claim 1 wherein the plurality of interferometers are Mach-Zehnder interferometers.

5. The multi-path interferometric sensor of claim 1 wherein the plurality of interferometers are micro ring resonators.

6. The multi-path interferometric sensor of claim 1 and further comprising a plurality of splitters for splitting the optical signal into the portions.

7. The multi-path interferometric sensor of claim 1 and further comprising a plurality of combiners for combining the plural portions of the optical signal before being received by the detector.

8. The multi-path interferometric sensor of claim 1 consisting of only a single detector.

9. A multi-path interferometric sensor comprising:
   a single light source for producing an optical signal, wherein the light source is suitably configured for wavelength scanning through a range of wavelengths on a periodic basis;
   surface waveguides defining a multi-path interferometer, wherein:
   a) the multi-path interferometer includes a plurality of sensing branches and a reference branch, each of which sensing branches and reference branch receive a portion of the optical signal;
   b) each of the sensing branches includes a sensing window in which a portion of a cladding of the waveguide defining the sensing branch is thinned relative to the cladding of the waveguide defining the reference branch;
   c) each of the sensing branches has a length that is different from one another and different from the reference branch;
   d) the portion of the optical signal received by each sensing branch and the reference branch is characterized by a different modulation frequency as a consequence of the different lengths of each sensing branch and the reference branch; and
   a single detector for receiving the portion of the optical signal from each sensing branch and the reference branch.

10. The multi-path interferometric sensor of claim 9 wherein the single light source is a vertical cavity surface emitting laser.

11. The multi-path interferometric sensor of claim 10 wherein the vertical cavity surface emitting laser emits light at a wavelength of 850 nanometers.

12. The multi-path interferometric sensor of claim 9 and further comprising a plurality of splitters for splitting the optical signal into the portions.

13. The multi-path interferometric sensor of claim 9 and further comprising a plurality of combiners for combining the plural portions of the optical signal before being received by the detector.

* * * * *